US009731146B2

(12) United States Patent
Rietzel

(10) Patent No.: US 9,731,146 B2
(45) Date of Patent: Aug. 15, 2017

(54) METHOD FOR DETERMINING AN IRRADIATION PLAN

(75) Inventor: Eike Rietzel, Weiterstadt (DE)

(73) Assignee: Siemens Aktiengesellschaft, München (DE)

( * ) Notice: Subject to any disclaimer, the term of this patent is extended or adjusted under 35 U.S.C. 154(b) by 1125 days.

(21) Appl. No.: 12/874,918

(22) Filed: Sep. 2, 2010

(65) Prior Publication Data

US 2011/0065974 A1 Mar. 17, 2011

(30) Foreign Application Priority Data

Sep. 7, 2009 (DE) ........................ 10 2009 040 390

(51) Int. Cl.
*A61N 5/00* (2006.01)
*A61N 5/10* (2006.01)

(52) U.S. Cl.
CPC ............ *A61N 5/103* (2013.01); *A61N 5/1031* (2013.01); *A61N 5/1037* (2013.01); *A61N 5/1038* (2013.01); *A61N 5/1039* (2013.01)

(58) Field of Classification Search
CPC .... A61N 5/103; A61N 5/1031; A61N 5/1082; A61N 5/1083; A61N 5/1084; A61N 2005/1032; A61N 2005/1034; A61N 2005/1035; A61N 5/1036; A61N 5/1037; A61N 5/1038; A61N 5/1039;
(Continued)

(56) References Cited

U.S. PATENT DOCUMENTS 5,926,568 A * 7/1999 Chaney et al. ............... 382/217
8,306,185 B2 * 11/2012 Bal et al. ........................ 378/65
(Continued)

FOREIGN PATENT DOCUMENTS

WO WO 2005035061 A2 4/2005

OTHER PUBLICATIONS

German Office Action dated Apr. 6, 2010 for corresponding German Patent Application No. DE 10 2009 040 390.6 with English translation.

(Continued)

*Primary Examiner* — Charles A Marmor, II
*Assistant Examiner* — Shannon McBride
(74) *Attorney, Agent, or Firm* — Lempia Summerfield Katz LLC

(57) ABSTRACT

A method for determining an irradiation plan includes specifying a target volume to be irradiated and a condition to be fulfilled, and implementing a first optimization. Implementing the first optimization includes providing a first data record, in which the target volume is mapped, and determining a first parameter set for the irradiation planning by implementing a first optimization algorithm. The first parameter set is optimized with respect to the condition to be fulfilled by using the first data record. The method also includes implementing a second optimization that includes providing a second data record that has a higher resolution than the first data record, determining a second parameter set by implementing a second optimization algorithm. The second parameter set is optimized with respect to the condition to be fulfilled by using the second data record and using the first parameter set. The method also includes generating an irradiation planning data record from the second parameter set.

21 Claims, 2 Drawing Sheets

(58) Field of Classification Search
CPC .......... A61N 2005/1041; A61N 5/1077; A61N 5/1078; A61N 5/1079; A61N 5/1081
USPC ..................... 600/1–6; 378/65; 128/897–899
See application file for complete search history.

(56) References Cited

U.S. PATENT DOCUMENTS

| | | | | |
|---|---|---|---|---|
| 2003/0219098 | A1 | 11/2003 | McNutt et al. | |
| 2006/0078086 | A1 | 4/2006 | Riley et al. | |
| 2007/0003011 | A1 | 1/2007 | Lane | |
| 2007/0081629 | A1 | 4/2007 | Yin et al. | |
| 2010/0081857 | A1* | 4/2010 | Georgi et al. | 600/1 |

OTHER PUBLICATIONS

European Search Report dated Oct. 4, 2010 for corresponding European Patent Application No. EP 10168809.1-2305 with English translation.

Lim, Jinho, "Optimization in Radiation Treatment Planning," Dissertation, University of Wisconsin-Madison, 2002, pp. 78-119.

Scherrer, A. et al., "IMRT planning on adaptive volume structures—a decisive reduction in computational complexity," Physics in Medicine and Biology 50, 2005, pp. 2033-2053.

Tsogtbaatar, Logi, "Multiresolution;Optimierung: Anwendbarkeit für die Einstrachlrichtungsoptimierung in der IMRT," Fachhochschule Giessen Friedberg, Institut für Medizinische Physik und Strahlenschutz, Tätigkeitsbericht, 2007, 3 pages.

* cited by examiner 10
12
13
14
15
16
18
20
22
24
26
28
30
32
34
36
38
41
41
42
44
46

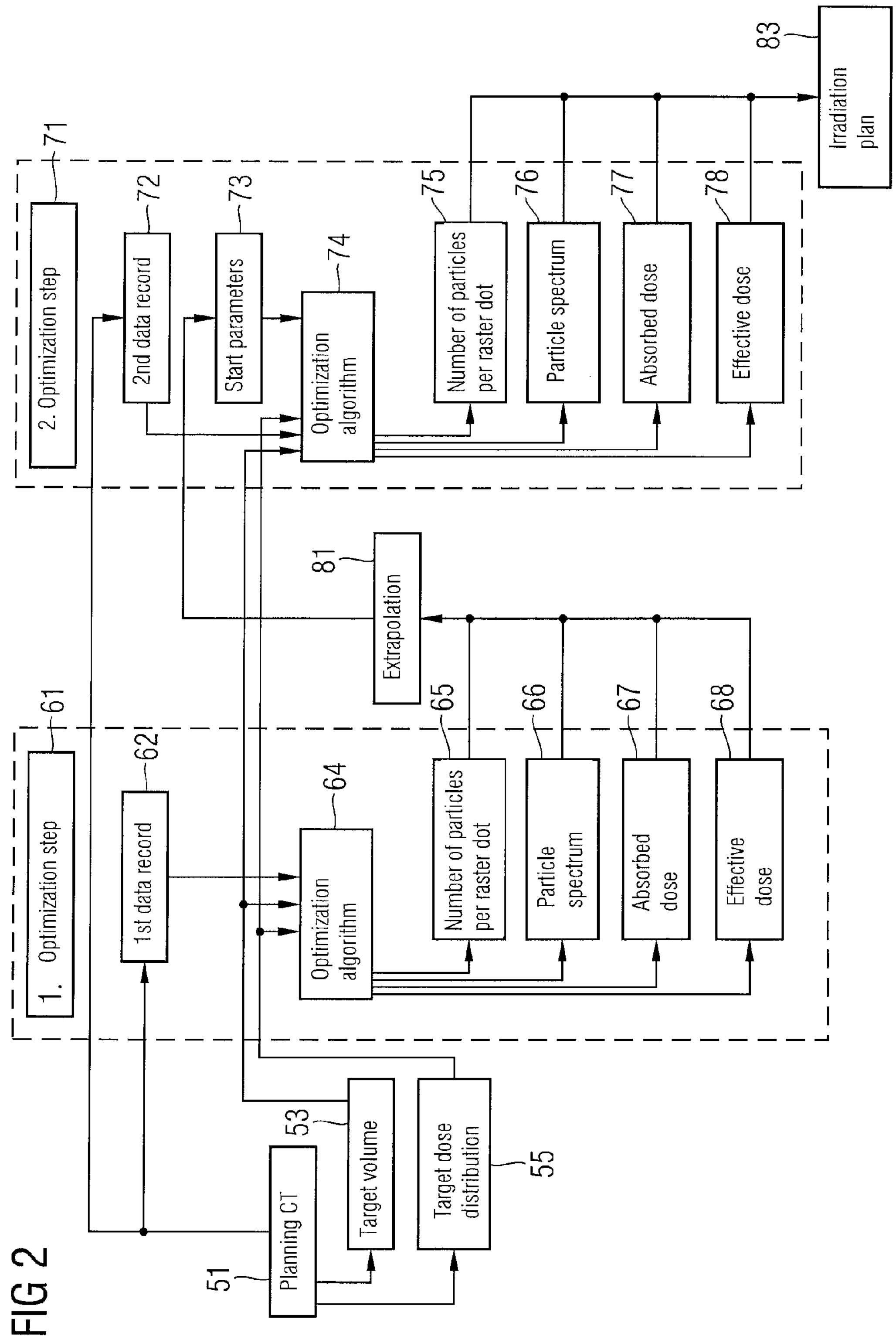
FIG 2
51
Planning CT
53
Target volume
55
Target dose distribution
61
1. Optimization step
62
1st data record
64
Optimization algorithm
65
Number of particles per raster dot
66
Particle spectrum
67
Absorbed dose
68
Effective dose
81
Extrapolation
71
2. Optimization step
72
2nd data record
73
Start parameters
74
Optimization algorithm
75
Number of particles per raster dot
76
Particle spectrum
77
Absorbed dose
78
Effective dose
83
Irradiation plan

METHOD FOR DETERMINING AN IRRADIATION PLAN

This application claims the benefit of DE 10 2009 040 390.6, filed on Sep. 7, 2009, which is hereby incorporated by reference.

BACKGROUND

The present embodiments relate to a method for determining an irradiation plan.

Particle therapy is an established method for treating tissue (e.g., tumor diseases). Irradiation methods, as are used in particle therapy, are however also used in non-therapeutic fields. These non-therapeutic fields include, for example, research work for product development within the scope of particle therapy, the research work being performed, for example, on non-living phantoms or bodies or the irradiation of materials.

In these applications, charged particles such as, for example, protons or carbon ions or other ions are accelerated to high energies, shaped to form a particle beam and guided to one or more irradiation rooms by way of a high energy beam transportation system. In the irradiation room, the target volume to be irradiated is irradiated with the particle beam.

Irradiation methods referred to as scanning methods are known. With these methods, a particle beam with a small diameter compared to the target volume is guided successively to a plurality of destinations in the target volume; the target volume is "scanned" by the particle beam.

Methods of "inverse" irradiation planning are likewise known. With methods of this type, an irradiation target to be reached (e.g., a target volume to be irradiated, organs to be protected and a target dose to be achieved) is specified by a user. It is then determined how this specification can be implemented during an irradiation (i.e., how the parameters, with which an irradiation process can be controlled and which finally effect the dose deposition, are to be adjusted). For example, the dose portion to be applied, the direction from which the dose portion is to be applied and the area of the target volume to which the dose portion is to be applied are determined. The parameters that characterize the dose distribution depend on one another in a complex fashion. An inverse irradiation planning is thus usually implemented with an optimization algorithm, which takes these dependencies into account.

SUMMARY AND DESCRIPTION

The present embodiments may obviate one or more of the drawbacks or limitations in the related art. For example, in one embodiment, a method for irradiation planning that allows a rapid calculation of an irradiation plan, may be specified.

One embodiment of a method for determining an irradiation plan includes specifying a target volume to be irradiated and a condition to be fulfilled and implementing a first optimization. Implementing the first optimization includes providing a first data record, in which the target volume is mapped, and determining a first parameter set for the irradiation planning by implementing a first optimization algorithm. The first parameter set is optimized with respect to the condition to be fulfilled by using the first data record. The method also includes implementing at least one further optimization. Implementing the at least one further optimization includes providing a further data record that has a higher resolution than the first data record, determining a further parameter set for the irradiation planning by implementing a further optimization algorithm. The further parameter set is optimized with respect to the condition to be fulfilled by using the further data record and using the first parameter set. The method also includes generating an irradiation planning data record from the further parameter set.

The present embodiments relate to an irradiation planning method, in which a plurality of optimizations is implemented one after the other.

The target volume to be irradiated and the condition to be fulfilled may be specified by a user. The condition to be fulfilled may be a specification, for example, that characterizes the dose distribution of the target volume to be achieved and other volumes to be protected.

The parameter set that is optimized and determined by the optimizations may be stored in an irradiation planning data record and is used to control an irradiation system accordingly, so that a corresponding irradiation of the target volume fulfills the condition to be fulfilled as well as possible.

A parameter set of this type may include the number of dose depositions to be implemented one after the other, the respective beaming directions and/or the dose to be applied in each instance. With a method for irradiation planning for a particle beam that is to be applied in the scanning method, in which the particle beam is to be controlled successively at several destinations in the target volume, the parameter set may include values that identify the number of particles to be applied per destination.

The parameter set may be used directly or indirectly to control an irradiation system, depending on the embodiment of the irradiation system (e.g., after a corresponding interpretation by a control algorithm and conversion into control commands).

The optimization acts differ from one another in that the resolution of the data record, which underlies the respective act, is successively higher and the calculation and implementation of the optimization acts thus becomes successively more complex and more expensive.

The parameter act, which is determined in a preceding optimization act, may still be determined with comparatively little computing time, since the resolution of the data record is minimal by comparison with subsequent steps. In the methods of the present embodiments, this parameter act is incorporated into the subsequent optimization. An irradiation planning method designed in this way reaches the target more rapidly and, despite several optimization acts, with less computing outlay than methods that use a highly resolved data record from the start and directly determine the optimum of the parameter values with the aid of the highly resolved data record.

The use of the parameter set, which has been determined and optimized in a previously implemented optimization, is used here to influence the subsequent optimizations (i.e., to channel and guide the optimizations in one direction). The optimization algorithm, which is used in the subsequent optimization, will consequently use fewer iterations to achieve the target and to determine the optimum for the parameter set.

Start values that influence the subsequent optimization may be determined from the parameter set. These start values already represent a good approximation of the parameter values that are to be determined and optimized in the subsequent optimization. Fewer iterations in the optimization algorithm, when compared with an optimization algorithm where these start values are not used, are needed in the subsequent optimization in order to determine the further parameter set. For this reason, the optimization algorithm may be rapidly implemented even in the case of a more highly resolved data record, since the start values may be slightly modified and adjusted.

The optimization algorithm used in the first optimization and the further optimization algorithm used in the further optimization may be the same or different optimization algorithms.

In one embodiment, a dose absorbed by the target volume may be determined in the optimization acts. In one embodiment, the condition to be achieved may also be an absorbed target dose to be achieved. Parameter values, which are used in one of the optimization acts to determine the absorbed dose, may be extrapolated to a more highly resolved data record. The more highly resolved data record is used in one of the subsequent optimizations.

The method is advantageous when an effect of the dose absorbed by the target volume (i.e., an effective dose) is determined in the optimization acts. In one embodiment, the condition to be achieved may be a target dose and/or effect on the target volume to be achieved. Parameter values, which may be used in one of the optimization acts to determine the effective dose, may be extrapolated to a more highly resolved data record. The more highly resolved data record is used in one of the subsequent optimization acts.

An effect of the particle beam of this type may be characterized by the relative biological efficiency (RBW). The calculation of the effect is very computer-intensive (e.g., in the case of particle beams with particles that are heavier than protons) as a result of the complex interaction with the target volume. The methods of the present embodiments, which operate with gradually higher resolutions, may result in a considerable shortening of the computing time. With the calculation of the effective dose and/or effect of the dose absorbed by the target volume, the particle spectrum generated in a position-dependent fashion by the particle beam is used, for example.

The parameter set, which is determined and optimized in the optimization acts, may include further values that are not used directly or indirectly to control an irradiation system but are used to calculate the dose distribution to be deposited.

Parameter values of this type may identify the particle spectrum that is expected to be generated by the particle beam to be applied. The generated particle spectrum depends on the anatomy of the target volume and on the interaction of the particle beam with the anatomy of the target volume. The generated particle spectrum may also be dependent on a location (e.g., the generated particle spectrum changes from voxel to voxel of the data record). The particle spectrum may be calculated comparatively rapidly with a low-resolution data record, while the calculation in the case of a higher-resolution data record is time-consuming and expensive as a result of the complex interaction of the particle beam with the target volume.

In one embodiment of the method, a particle spectrum generated by the beam to be applied is calculated in the optimization acts as a function of the location in the target volume (e.g., with a resolution that corresponds to the resolution of the data record that is used in the respective optimization act). This calculation may take place voxel by voxel. In the case of a low-resolution data record, the calculation thus demands less time than with a high-resolution data record.

The particle spectrum calculated in one of the preceding optimization acts may be extrapolated to the more highly resolved data record, which is used in a subsequent optimization act. Start values for the optimization algorithm may be determined from the particle spectrum calculated in one of the optimization acts during one of the subsequent optimization acts (e.g., using the extrapolation). An extrapolation may be implemented comparatively rapidly and easily.

In a data record that is used in a preceding optimization act, the number of voxels is less than the number of voxels of a data record that is used in one of the subsequent optimization acts. Significant savings in terms of optimization time result therefrom, since the smaller number of voxels permits a significantly quicker calculation and implementation of the optimization algorithm. With this optimization, the particle spectra occurring in the voxels (e.g., the complete particle spectra) are calculated. These particle spectra are may be used to calculate the effect of the particle beam on the target volume in the case of a particle beam (i.e., the effective dose and/or the relative biological values). If these particle spectra in each of the voxels are extrapolated to a higher resolution, very good start values are already predetermined for the further optimization, which may be implemented on a higher resolved data record. In the next optimization act, comparatively fewer iterations are thus used in order to further optimize the parameter set.

In one embodiment of the method, the data records with different resolutions, which are used in the optimization acts, are determined from a single planning data record. This may be a planning CT, for example. The different data records may be calculated from the single planning data record by a plurality of adjacent voxels being differently combined to form a larger voxel, for example using averaging.

An irradiation planning facility includes a computer unit having an input device and an output device, with the computer unit being configured to implement one embodiment of the method for determining an irradiation plan.

An irradiation system (e.g., a particle therapy system) includes an irradiation planning facility of this type and a control apparatus for controlling the particle therapy system. The particle therapy system may control the irradiation system using an irradiation planning data record created according to one embodiment of the method for determining an irradiation plan.

Although present embodiments have a particularly advantageous effect in the case of particle therapy systems, the present embodiments may also be used with an irradiation using x-ray radiation.

The preceding and subsequent embodiments relate to features, the mode of operation and advantages of which relate to the apparatus category and method category respectively, without this being explicitly mentioned in each instance. The individual features disclosed here may also be of significance to the present embodiments in other combinations than those shown.

BRIEF DESCRIPTION OF THE DRAWINGS

FIG. 2 shows a schematic overview of one embodiment of a method for determining an irradiation plan.

DETAILED DESCRIPTION OF THE DRAWINGS

Figure 1:
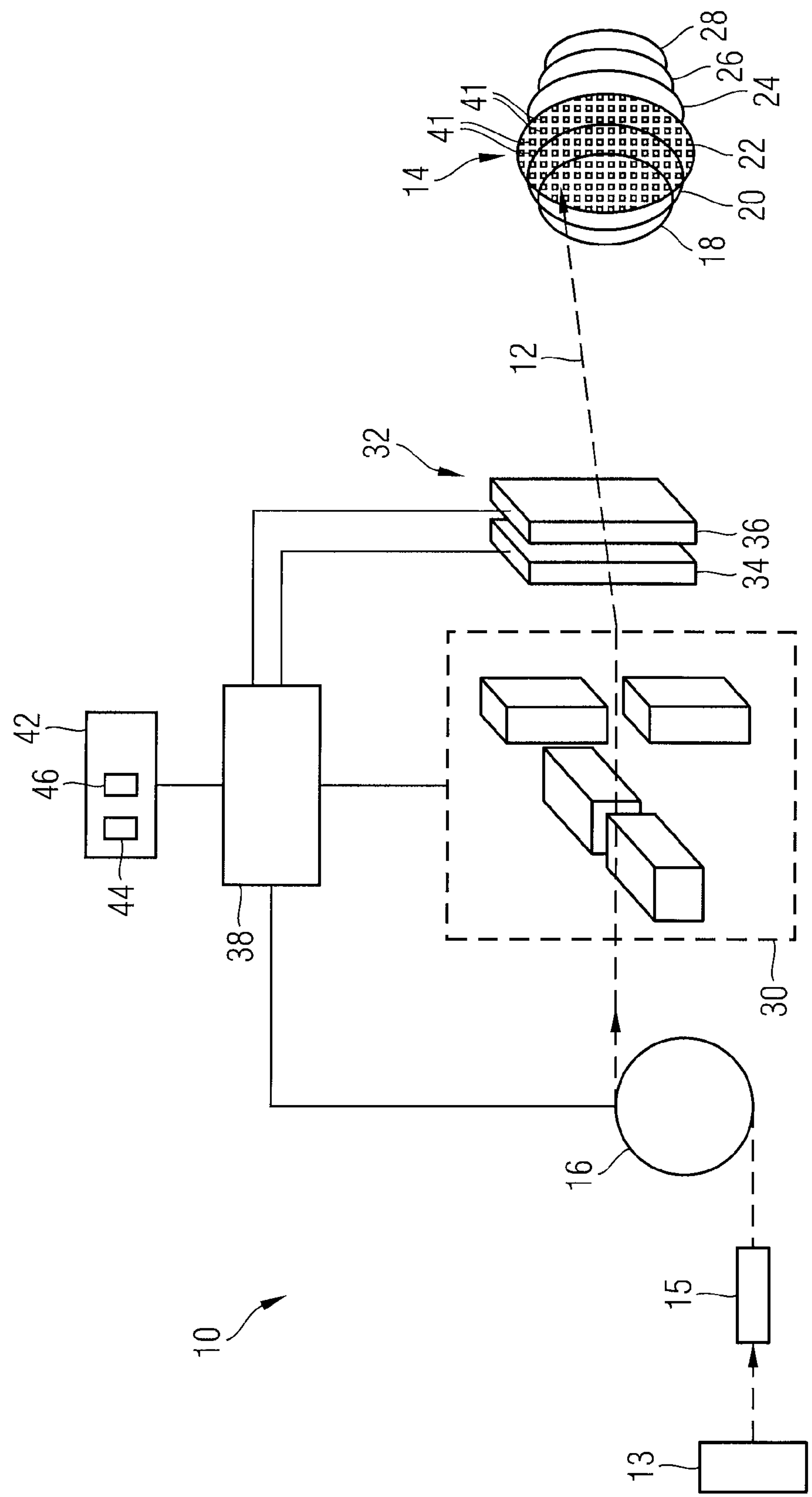
FIG. 1 shows a schematic representation of a particle therapy system.

FIG. 1 shows a highly schematic representation of a design of an irradiation system structured as a particle therapy system 10. The particle therapy system 10 is used to irradiate a target volume, which may be positioned accordingly with a positioning apparatus, with a beam including particles (e.g., a particle beam 12). For example, a tumor-diseased tissue in a patient may be irradiated with the particle beam 12. The particle beam system 10 may also be used to irradiate a non-living body (e.g., a water phantom or other phantoms). The irradiation of the water phantom may take place before and/or after completion of an irradiation of a patient to monitor and verify irradiation parameters, for example. Other bodies such as experimental setups including, for example, cell cultures, or bacteria cultures may also be irradiated with the particle beam 12.

The particle therapy system 10 may include a particle source 13 and an accelerator unit (e.g., a synchrotron 16 and preaccelerator 15 or a cyclotron or other accelerator), which provides a particle beam 12 with the energy needed for irradiation purposes. Particles such as protons, pions, helium ions, carbon ions or ions of other elements may, for example, be used as particles. A particle beam 12 may, for example, have a beam diameter of 3-10 mm. The particle beam 12 is guided to an irradiation room, in which the target volume 14 is located.

Isoenergy layers 18, 20, 22, 24, 26 and 28 are shown in the target volume 14 to be irradiated. An isoenergy layer 18, 20, 22, 24, 26 or 28 corresponds, in each case, to the penetration depth of the Bragg peak for a certain energy of the particle beam 12.

A raster scan method may be used as a scanning method. In the raster scan method, the particle beam 12 is guided from one destination 41 to another destination 41 without having to shut down when transitioning from one destination to the next. Spot scanning methods with shutdown of the particle beam may be used between the individual destinations, or other scanning methods such as, for example, continual scanning methods may be used. FIG. 1 shows a schematic illustration of the scanning method with the aid of a plurality of destinations 41. The plurality of destinations 41 are shown, in part, in the target volume 14 structured layer-by-layer. The plurality of destinations is reached successively with the particle beam 12.

For implementing the scanning method, a scanning apparatus 30 may be provided with a number of deflection magnets in two orthogonal directions, which allow the particle beam 12 to be guided from destination 41 to destination 41.

A beam monitoring facility 32, with which a beam quality of the particle beam 12 may be monitored, may include, for example, an ionization chamber 34 to monitor the number of particles applied by the particle beam 12 and a location measuring chamber 36 to monitor the location of the particle beam 12 (measuring apparatuses 34, 36).

A control facility 38 controls the particle therapy system 10. The control facility 38 may control the accelerator 15, 16 to provide a beam with a desired intensity, guide the beam according to an irradiation plan with the scanning apparatus 30 and evaluate the measurement data of the beam monitoring facility 32 for monitoring the beam quality. The control facility 38 may select one of a number of measurement ranges in which the beam monitoring facility 32 and/or the measuring apparatuses 34, 36 thereof, is to be operated. The control facility 38 may be divided into a number of sub units that are networked with one another (not shown in FIG. 1 for simplification).

An irradiation planning facility 42 (e.g., a computing unit) includes an input device 44 and an output device 46 for interaction with a user. The irradiation planning facility 12 is connected to the control facility 38 such that an irradiation plan, which has been created with the irradiation planning facility 42, may be executed on the particle therapy system 10.

A particle therapy system 10 of this type is known in the prior art.

An irradiation plan may however be advantageously determined on the irradiation planning facility 42, if one of the methods of the present embodiments is executed thereon as explained below.

FIG. 2 shows a schematic overview of one embodiment of a method for determining an irradiation plan.

At act 51, a planning CT is provided. With the aid of a computer unit, which includes an input device (e.g., a mouse, a keyboard) and an output device (e.g., monitor), a user of the may mark the target volume to be irradiated (act 53). The user may also determine in this act which regions in the object to be irradiated are to be spared, as much as possible, a dose deposition (e.g., organs at risk (OAR)). The user specifies a target dose distribution, with which the target volume is to be irradiated (act 55).

A first optimization subsequently implemented (act 61). The basis of this first optimization forms a first data record, which maps the target volume in a similar fashion to the planning CT. The first data record may have a significantly smaller resolution than the planning CT (act 62). The first data record may have been generated from the planning CT, for example.

The first data record forms the basis of a first optimization algorithm, with which the parameters for irradiation are determined and optimized (act 64).

The specifications performed by the user with respect to the target volume and target dose distribution are also incorporated into the first optimization algorithm. The first optimization algorithm may be a known optimization algorithm that is already used within the scope of inverse irradiation planning. An optimization algorithm of this type may be based on a recursive method.

A first parameter set for the irradiation plan is optimized with the first optimization algorithm. This includes, for example, the number of particles to be applied per destination in the target volume (act 65), the particle spectrum generated by the particle beam in the target volume (act 66), the dose absorbed in the target volume (act 67). The first parameter set may also include the effect generated by the particle beam in the target volume (the effective dose) (act 68).

With the first optimization algorithm of the first optimization, the first parameter set is optimized until the target setting with respect to the target dose distribution in the target volume is achieved as accurately as possible. As the first data record has a low resolution, the first parameter set may not completely fulfill the requirements. A comparatively small computing time is required herefor, in order to achieve a first result for the first parameter set with the first optimization algorithm.

The first parameter set is further optimized (act 71) in a second optimization.

To this end, a second data record is generated from the planning CT, in which the target volume is likewise mapped. The second data record has a higher resolution by comparison with the first data record (act 72).

Similarly to the first optimization, the second data record forms the basis of the optimization algorithm of the second optimization step. The specifications of the user with respect to the target volume and the target dose distribution are incorporated into the optimization algorithm of the second optimization (act 74). Start values are generated from the first parameter set, which was determined in the first optimization (act 73). The start values are likewise incorporated into the optimization algorithm of the second optimization and represent the starting point for the optimization. Since these values already represent a first approximation for the parameters to be optimized, the second optimization algorithm requires comparatively little time and computing power in order to adjust the first parameter set to the second data record and to find a second parameter set that better fulfills the specifications of the user than the first parameter set.

To generate the start values for the optimization algorithm of the second optimization, the first parameter set may be extrapolated from the first optimization onto the second data record (act 81).

The second parameter set of the second optimization may include similar parameters to the first parameter set such as, for example, the number of particles to be applied in the target volume per destination (act 75), the particle spectrum that is generated by the particle beam in the target volume (act 76), the dose absorbed in the target volume (act 77) and the effective dose of the particle beam in the target volume (act 78).

In one embodiment, one or more further optimization step/s may be implemented similarly to the second optimization (not shown in FIG. 2 for the sake of simplicity). The optimizations may be repeated and continued until the optimization on a data record has taken place with a sufficiently precise resolution. An irradiation plan may be created from the parameter set that is determined and optimized in this way (act 83).

It may be inferred from the irradiation plan (e.g., a data record) how an irradiation has taken place in order to achieve the desired dose deposition in the target volume. This irradiation plan may be read in and implemented by the control apparatus of an irradiation system in order to control the irradiation system for correct irradiation of the target volume.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A planning method for a scanning method for determining an irradiation plan, the planning method comprising:

identifying a planning data record representing a target volume to be irradiated and generated by an imaging, device;

specifying the target volume to be irradiated and a condition to be fulfilled, the target volume having a size and a shape;

implementing a first optimization that comprises:

providing a first data record, providing the first data record comprising generating the first data record from the planning data record generated by the imaging device;

mapping the target volume having the size and the shape in the first data record; and determining a first parameter set for irradiation planning by implementing a first optimization algorithm, in which the first parameter set is optimized with respect to the condition to be fulfilled using the first data record;

implementing a second optimization that comprises:

providing a second data record, which has a higher resolution than the first data record, providing the second data record comprising generating the second data record from the planning data record generated by the imaging device;

mapping the target volume having the size and the shape in the second data record; and determining a second parameter set for the irradiation planning by implementing a second optimization algorithm, the implementing of the second optimization algorithm comprising optimizing the second parameter set with respect to the condition to be fulfilled using the second data record and the first parameter set;

generating an irradiation planning data record using the second parameter set; and successively controlling a particle beam to destinations in the target volume based on the irradiation planning data record.

2. The method as claimed in claim 1, wherein implementing the second optimization comprises determining start values for the second optimization algorithm from the first parameter set.

3. The method as claimed in claim 2, wherein implementing the first optimization and implementing the second optimization both comprise calculating a particle spectrum generated by a beam to be applied as a function of the location in the target volume.

4. The method as claimed in claim 3, wherein the particle spectrum calculated in the first optimization is extrapolated onto the second data record, which is used in the second optimization step.

5. The method as claimed in claim 4, wherein the start values for the second optimization algorithm are determined from the particle spectrum calculated in the first optimization.

6. The method as claimed in claim 3, wherein the start values for the second optimization algorithm are determined from the particle spectrum calculated in the first optimization.

7. The method as claimed in claim 2, wherein implementing the first optimization and implementing the second optimization both comprise determining a dose absorbed by the target volume.

8. The method as claimed in claim 2, wherein the condition to be fulfilled is a dose distribution to be achieved in the target volume.

9. The method as claimed in claim 1, wherein implementing the first optimization and implementing the second optimization both comprise determining a dose absorbed by the target volume.

10. The method as claimed in claim 9, wherein implementing the first optimization and implementing the second optimization both comprise determining an effect of the dose absorbed by the target volume as an effective dose.

11. The method as claimed in claim 10, wherein implementing the first optimization and implementing the second optimization both comprise calculating a particle spectrum generated by a beam to be applied as a function of a location in the target volume.

12. The method as claimed in claim 9, wherein implementing the first optimization and implementing the second optimization both comprise calculating a particle spectrum generated by a beam to be applied as a function of a location in the target volume.

13. The method as claimed in claim 9, wherein the condition to be fulfilled is a dose distribution to be achieved in the target volume.

14. The method as claimed in claim 1, wherein the first parameter set and the second parameter set include values that characterize a number of particles to be applied per destinations.

15. The method as claimed in claim 14, wherein the condition to be fulfilled is a dose distribution to be achieved in the target volume.

16. The method as claimed in claim 1, wherein the condition to be fulfilled is a dose distribution to be achieved in the target volume.

17. The method as claimed in claim 1, wherein implementing the first optimization and implementing the second optimization both comprise calculating a particle spectrum generated by a beam to be applied as a function of a location in the target volume.

18. The method as claimed in claim 1, wherein identifying the planning data record representing the target volume comprises generating, with an imaging device, a planning computed tomography (CT) data record.

19. The method as claimed in claim 1, wherein the determined first parameter set for the irradiation planning comprises a number of particles to be applied per destination in the target volume, a particle spectrum generated by a particle beam in the target volume, a dose absorbed in the target volume, or an effective dose in the target volume.

20. An irradiation planning facility included in an irradiation system comprising a control apparatus for controlling the irradiation system, the irradiation planning facility comprising:

a computer unit with an input device and an output device, the computer unit being configured for:

identifying a planning data record representing a target volume to be irradiated and generated by an imaging device;

specifying the target volume to be irradiated and a condition to be fulfilled, the target volume having a size and a shape;

implementing a first optimization that comprises:

providing a first data record, providing the first data record comprising generating the first data record from the planning data record generated by the imaging device;

mapping the target volume having the size and the shape in the first data record; and determining a first parameter set for the irradiation planning by implementing a first optimization algorithm, in which the first parameter set is optimized with respect to the condition to be fulfilled using the first data record;

implementing a second optimization that comprises:

providing a second data record, which has a higher resolution than the first data record, providing the second data record comprising generating the second data record from the planning data record generated by the imaging device;

mapping the target volume having the size and the shape in the second data record; and determining a second parameter set for the irradiation planning by implementing a second optimization algorithm, the implementing of the second optimization algorithm comprising optimizing the second parameter set with respect to the condition to be fulfilled using the second data record and the first parameter set; and generating an irradiation plan data record using the second parameter set, wherein the control apparatus is configured to control a particle beam to destinations in the target volume based on the irradiation plan data record.

21. An irradiation system comprising:

an irradiation planning facility comprising a computer unit with an input device and an output device; and a control apparatus for controlling the irradiation system based on an irradiation plan, the irradiation plan being generated by:

identifying a planning data record representing a target volume to be irradiated and generated by an imaging device;

specifying the target volume to be irradiated and a condition to be fulfilled, the target volume having a size and a shape;

implementing a first optimization that comprises:

providing a first data record, providing the first data record comprising generating the first data record from the planning data record generated by the imaging device;

mapping the target volume having the size and the shape in the first data record;

determining a first parameter set for the irradiation planning by implementing a first optimization algorithm, in which the first parameter set is optimized with respect to the condition to be fulfilled using the first data record;

implementing a second optimization that comprises:

providing a second data record, which has a higher resolution than the first data record, providing the second data record comprising generating the second data record from the planning data record generated by the imaging device;

mapping the target volume having the size and the shape in the second data record;

determining a second parameter set for the irradiation planning by implementing a second optimization algorithm, the implementing of the second optimization algorithm comprising optimizing the second parameter set with respect to the condition to be fulfilled using the second data record and the first parameter set; and generating an irradiation plan data record using the second parameter set, wherein the control apparatus is configured to control a particle beam to destinations in the target volume based on the irradiation plan data record.

* * * * *